(12) United States Patent
Steward et al.

(10) Patent No.: US 7,179,249 B2
(45) Date of Patent: Feb. 20, 2007

(54) DIRECTIONAL NEEDLE INJECTION DRUG DELIVERY DEVICE AND METHOD OF USE

(75) Inventors: Jeffrey Steward, Lakewood, CO (US); Mina Chow, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 677 days.

(21) Appl. No.: 10/390,942

(22) Filed: Mar. 17, 2003

(65) Prior Publication Data

US 2003/0233065 A1 Dec. 18, 2003

Related U.S. Application Data

(62) Division of application No. 09/697,571, filed on Oct. 26, 2000, now Pat. No. 6,554,801.

(51) Int. Cl.
*A61M 31/00* (2006.01)
(52) U.S. Cl. .................. 604/500; 604/506; 604/509
(58) Field of Classification Search ............. 604/500, 604/506–509, 264, 523, 529; 128/898; 600/459–467, 600/424, 439, 470
See application file for complete search history.

(56) References Cited

U.S. PATENT DOCUMENTS

| | | | | |
|---|---|---|---|---|
| 4,375,818 A | * | 3/1983 | Suwaki et al. ............... 600/463 |
| 5,178,150 A | * | 1/1993 | Silverstein et al. ......... 600/463 |
| 5,190,046 A | * | 3/1993 | Shturman .................. 600/463 |
| 5,331,947 A | * | 7/1994 | Shturman .................. 600/115 |
| 5,443,457 A | * | 8/1995 | Ginn et al. ................ 604/528 |
| 5,464,395 A | | 11/1995 | Faxon et al. ............... 604/96 |
| 5,474,075 A | * | 12/1995 | Goldberg et al. .......... 600/463 |
| 5,499,630 A | * | 3/1996 | Hiki et al. ................ 600/461 |
| 5,713,363 A | * | 2/1998 | Seward et al. ............. 600/437 |
| 5,957,849 A | * | 9/1999 | Munro ...................... 600/459 |
| 5,997,497 A | * | 12/1999 | Nita et al. ................ 604/22 |
| 6,056,744 A | * | 5/2000 | Edwards ................... 606/41 |
| 6,102,867 A | * | 8/2000 | Dietz et al. ............... 600/461 |
| 6,186,947 B1 | * | 2/2001 | Ouchi ....................... 600/439 |
| 6,238,336 B1 | * | 5/2001 | Ouchi ....................... 600/160 |
| 6,283,951 B1 | * | 9/2001 | Flaherty et al. ............ 604/529 |
| 6,306,097 B1 | * | 10/2001 | Park et al. ................ 600/466 |
| 6,660,024 B1 | | 12/2003 | Flaherty et al. |

\* cited by examiner

*Primary Examiner*—LoAn H. Thanh
(74) *Attorney, Agent, or Firm*—Blakely, Sokoloff, Taylor & Zafman LLP

(57) ABSTRACT

The invention relates to an apparatus and method for imaging and mapping various structures located at a target area within a patient's lumen using conventional IVUS technology. The mapped images are used to accurately determine and control the location of the device within the lumen relative to the target area and/or target site. Once the drug delivery device is properly positioned within the lumen, additional ultrasonic images are generated and used to control the position and depth of penetration of a retractable needle of the device. Needle position can be precisely determined, both in relationship to the device as well as the target site for drug delivery. This allows accurate delivery of drug to the target site and, thus, enhanced treatment capabilities.

7 Claims, 8 Drawing Sheets

DIRECTIONAL NEEDLE INJECTION DRUG DELIVERY DEVICE AND METHOD OF USE

This application is a divisional application of U.S. patent application Ser. No. 09/697,571, which was filed on Oct. 26, 2000 now U.S. Pat. No. 6,554,801.

FIELD OF THE INVENTION

The present invention relates to an apparatus and method for imaging the position and location of a medical device in a patient. In particular, the present invention relates to a catheter based needle drug delivery device having ultrasound imaging technology that facilitates tracking of the catheter as it is positioned within the body of a patient.

BACKGROUND

As surgical techniques continue to progress and become less invasive, an increasing number of medical procedures are performed with the aid of a catheter. In general, a catheter is a flexible tube that is inserted into narrow openings within the body and is used to deliver and/or remove fluids or substances. An example of a medical procedure that utilizes a catheter is percutaneous transluminal coronary angioplasty (PTCA).

PTCA is a catheter-based technique whereby a balloon catheter is inserted into the blocked or narrowed coronary lumen of a patient. Once the balloon is positioned at the target site, the balloon is inflated causing dilation of the lumen. The balloon is deflated and the catheter is then removed from the target site thereby allowing blood to freely flow through the unrestricted lumen.

Although PTCA procedures aid in alleviating intraluminal constrictions, such constrictions or blockages reoccur in many cases. The cause of these recurring obstructions, termed restenosis, is due to the body's immune system responding to the trauma of the surgical procedure. As a result, drug therapies are often applied in combination with the PTCA procedure to avoid or mitigate the effects of restenosis at the surgical site. The drugs are delivered to the site via a needle housed within the catheter. The term "drug(s)," as used herein, refers to all therapeutic agents, diagnostic agents/reagents and other similar chemical/biological agents, including combinations thereof, used to treat and/or diagnose restenosis, thrombosis and related conditions.

Other procedures, such as those developed to control the effects and occurrence of angiogenesis, also utilize a catheter having a drug delivery needle. Angiogenesis is a process whereby new blood vessels are grown in the body for healing wounds and for restoring blood flow to tissues after injury or trauma. Angiogenesis occurs naturally in the body, both in normal states and in disease states. For example, in females, angiogenesis occurs during the monthly reproductive cycle to rebuild the uterus lining and to mature the egg during ovulation. In addition, angiogenic growth factors are also present during pregnancy to build the placenta and create the vessels necessary for circulation between the mother and fetus.

Angiogenesis also occurs in various disease states, such as cancer, diabetic blindness, age-related macular degeneration, rheumatoid arthritis, coronary artery disease, stroke, and other disorders. In cases of excessive angiogenesis, the new blood vessels feed diseased tissues, destroy normal tissues and, with respect to cancer, allow tumor cells to escape into the circulation and lodge in other organs. Conversely, insufficient angiogenesis causes inadequate blood vessel growth thereby impeding circulation which, in turn, potentially leads to tissue death.

Although angiogenesis occurs naturally in the body, various procedures have been developed to artificially control the occurrence and effects of angiogenesis. One such procedure is Percutaneous TransMyocardial Revascularization (PTMR). PTMR utilizes a laser catheter to create small channels in the diseased tissue. The channels re-establish direct blood flow to the tissue and allow oxygen-rich blood to saturate the oxygen-starved tissue. PTMR is generally used for the treatment of severe, end-stage coronary disease.

Another catheter-based procedure used to promote angiogenesis involves gene therapy. For this procedure, genetic material is delivered directly to the diseased area of the body via a catheter. In particular, genetic material, such as Vascular Endothelial Growth Factor (VEGF), is incorporated into gene delivery vehicles called vectors, which encapsulate therapeutic genes for delivery to the diseased cells. Many of the vectors currently in use are based on attenuated or modified versions of viruses. The vectors may also be synthetic versions in which complexes of DNA, proteins, or lipids are formed into particles capable of efficiently transferring genetic material. A needle injection catheter is used to deliver the vectors containing the genetic material to the appropriate cells of the patient in a safe and efficient manner.

These and other similar catheter-based procedures require accurate tracking of needle location as the catheter and needle are maneuvered through the system to the target site in the patient. Conventional catheter-based needle drug delivery devices utilize fluoroscopic imaging methods to track catheter and needle movement in the body of a patient. In general, a radiopaque coating is applied in a thin, dense layer on a portion of the catheter and/or needle that is then viewed utilizing a fluoroscope. However, this method is limited to visualizing device placement within the artery. This is a limitation when the target for the needle-born drug/therapy is outside the delivery vessel. Further, this method produces a planar (two-dimensional image) which may not be sufficient to accurately steer or track the location of the catheter through the body of the patient. In addition, due to inadequate fluoroscopic imaging resolution and limited mass/density of radiopaque material, these devices are also limited in their effectiveness to accurately position the catheter needle at the desired target site.

SUMMARY

In view of the above, there is a need to provide a catheter-based needle drug delivery device having retractable ultrasonic imaging features that increases imaging resolution and improves catheter tracking capabilities. It is also desirable that the catheter-based needle drug delivery device be used in combination with intravascular ultrasound (IVUS) technology for mapping needle position in the body of the patient. In particular, it is preferred that the ultrasound imaging features of the present device enable a user of the device to precisely determine needle position in relation to both the host catheter as well as the vessel wall and target site for drug delivery.

In accordance with various aspects of the present invention, the invention relates to an apparatus and method for imaging and mapping various structures located at a target area within a patient's lumen using conventional IVUS technology. The mapped images are used to accurately determine and control the location of the device within the lumen relative to the target area and/or target site. Once the drug delivery device is properly positioned within the lumen, additional ultrasonic images are generated and used to control the position and depth of penetration of a retractable needle of the device. Needle position can be precisely determined, both in relationship to the device as well as the target site for drug delivery. This allows accurate delivery of drug to the target site and, thus, enhanced treatment capabilities.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

DETAILED DESCRIPTION

Figure 1:
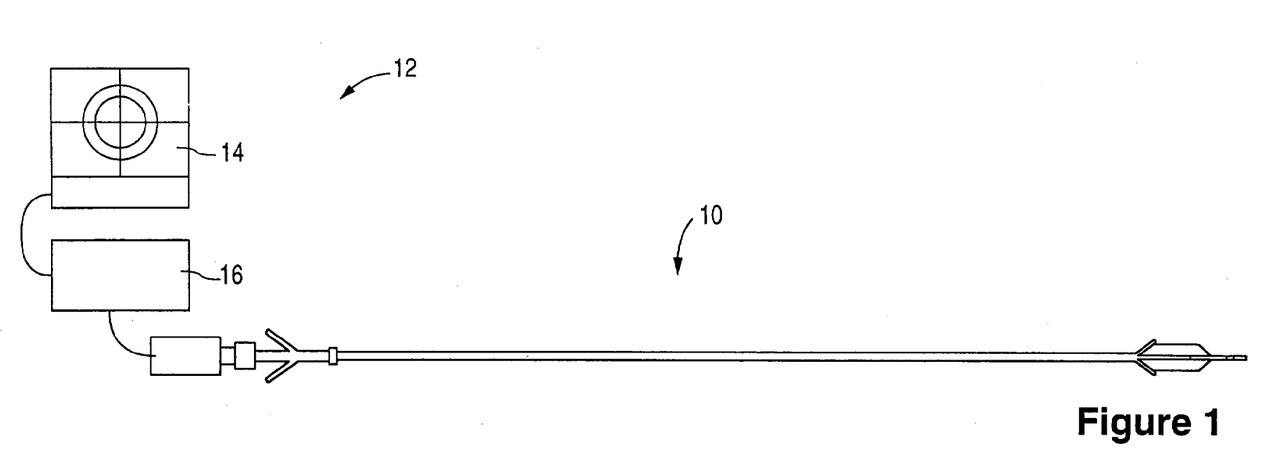
FIG. 1 is a perspective view of a catheter based needle drug delivery device and ultrasound imaging system.

An exemplary catheter-based needle drug delivery device 10 and ultrasonic imaging display system 12 are shown schematically in FIG. 1. The imaging display system 12 includes an image processor having a display 14 and a signal processor 16. Both the image processor 14 and signal processor 16 are general purpose processors of the type that are commonly used in connection with devices similar to that of the present invention. Additional disclosure of the ultrasonic imaging system 12 is discussed in further detail below.

Figure 2A:
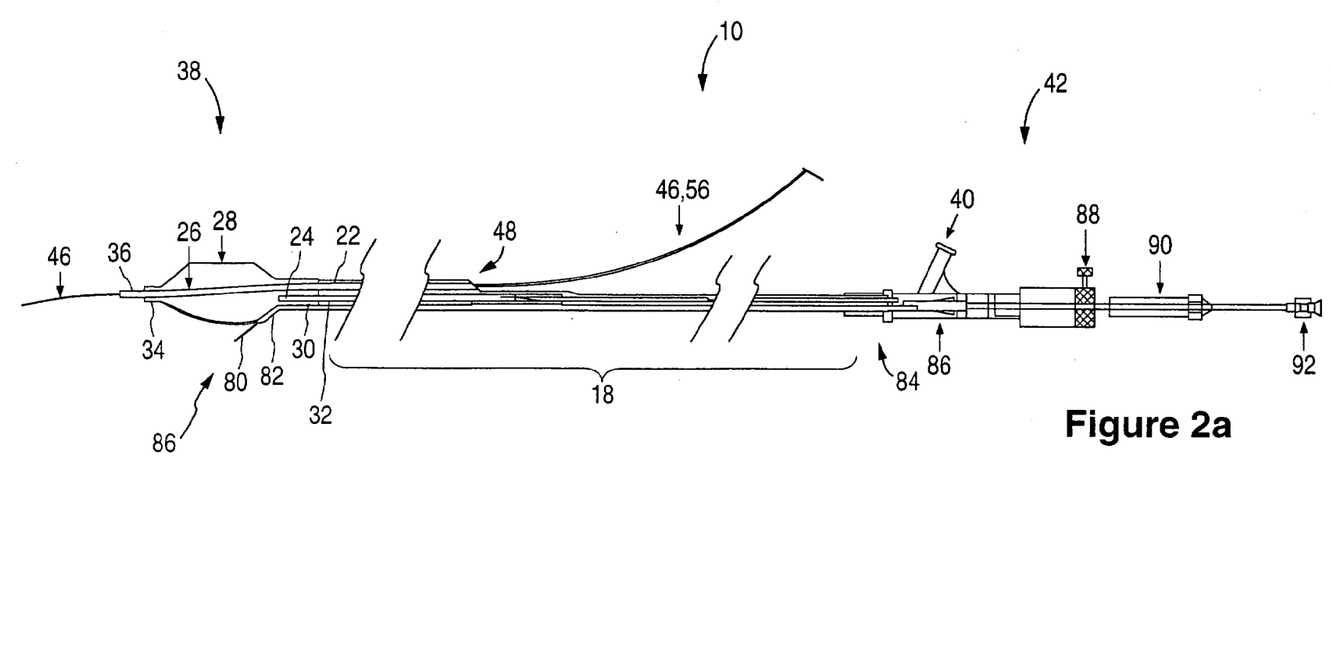
FIGS. 2a–2e are cross-sectional views of various embodiments of a catheter based needle drug delivery device.
Figure 2B:
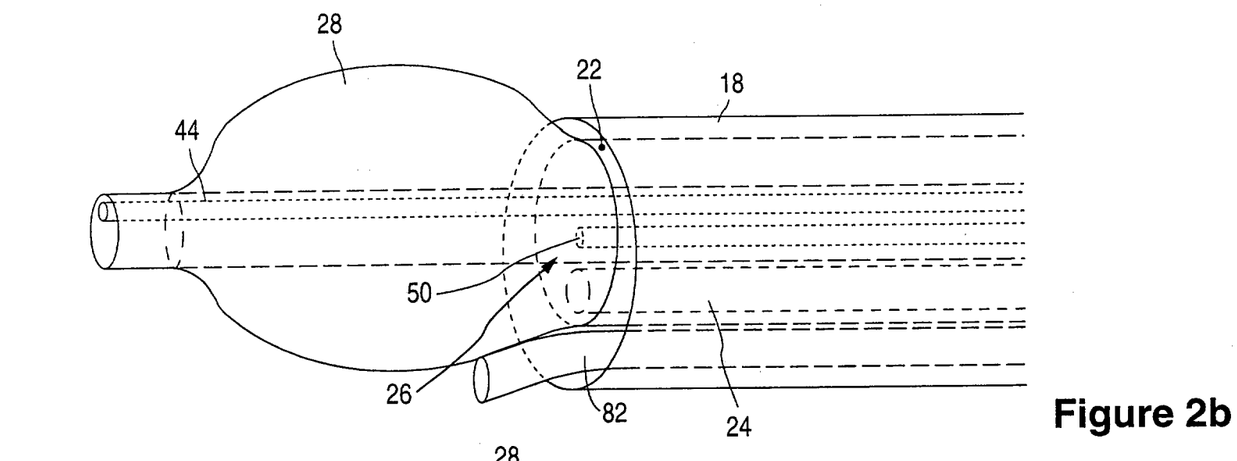

FIGS. 2a and 2b show cross-sectional views of the catheter-based needle drug delivery device 10. In general, the device 10 includes an elongate body 18 that surrounds a needle lumen 82 and an inner lumen 22. Housed within the inner lumen 22 are a fluid lumen 24 and an inner member 26 that also contains a guide wire lumen 44 and ultrasonic element lumen 50. An inflatable balloon 28 is attached to the inner lumen 22 and the inner member 26. In general, the proximal end 30 of the balloon 28 is attached to a distal end 32 of the inner lumen 22 and the distal end 34 of the balloon 28 is attached to the distal end 36 of the inner member 26. In the spirit of convenience and brevity, the device referenced in the text and figures of the present disclosure is configured according to the above-described design. However, it should be noted that other designs of the catheter-based needle drug delivery device are also within the scope of the claimed invention.

Figure 2C:
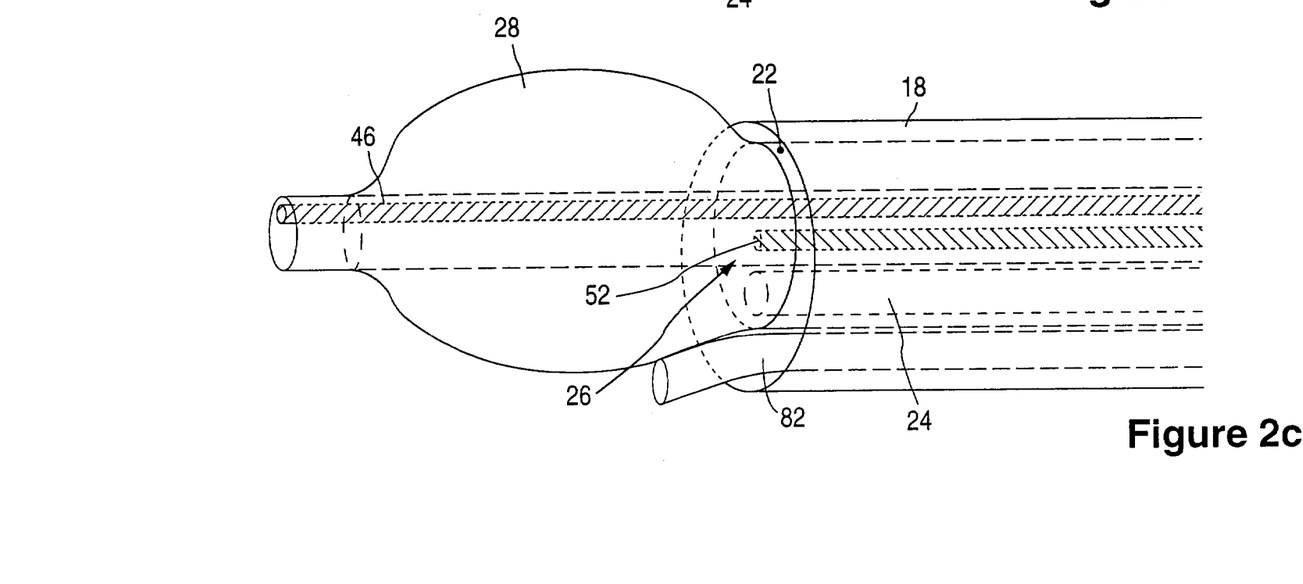

For example, in another embodiment of the device shown in FIG. 2c, both the guide wire 46 and retractable ultrasonic element 52 are housed within a single lumen, i.e. the inner member 26. The elongate body 18 surrounds an inner lumen 22 and a needle lumen 82. Housed within the inner lumen 22 are an inner member 26 and a fluid lumen 24. The inner member 26 surrounds the guide wire 46 and retractable ultrasonic element 52. An inflatable balloon 28 is attached to the inner lumen 22 and the inner member 26. In general, the proximal end of the balloon 28 is attached to the distal end of the inner lumen 22 and the distal end of the balloon 28 is attached to the distal end of the inner member 26.

Figure 2D:
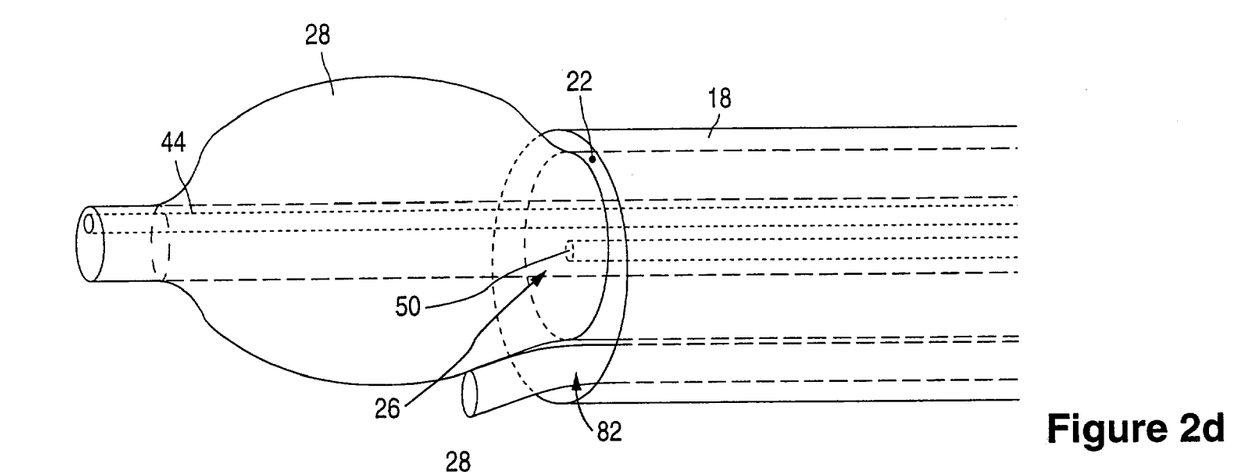
Figure 2E:
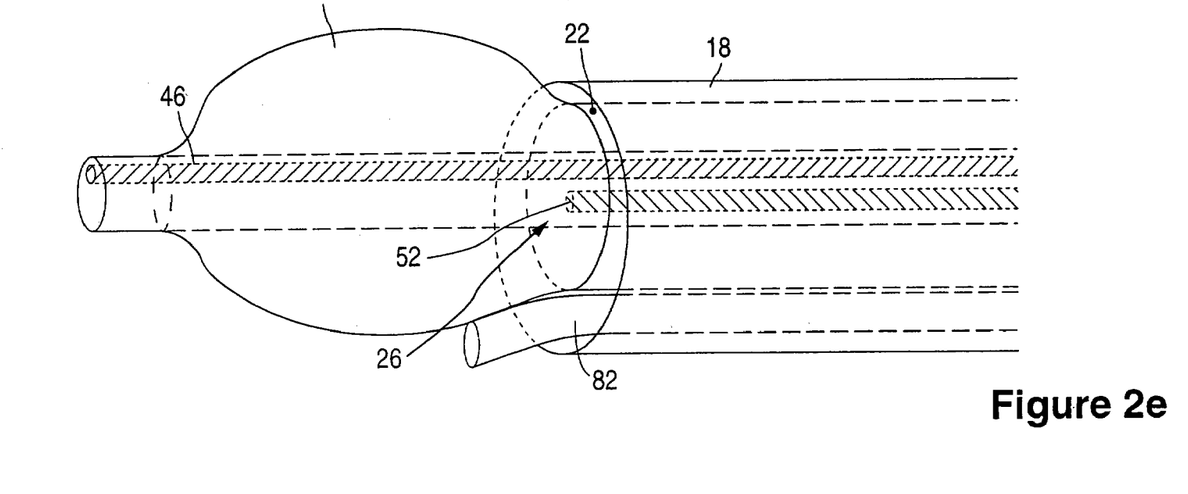
Figure 2F:
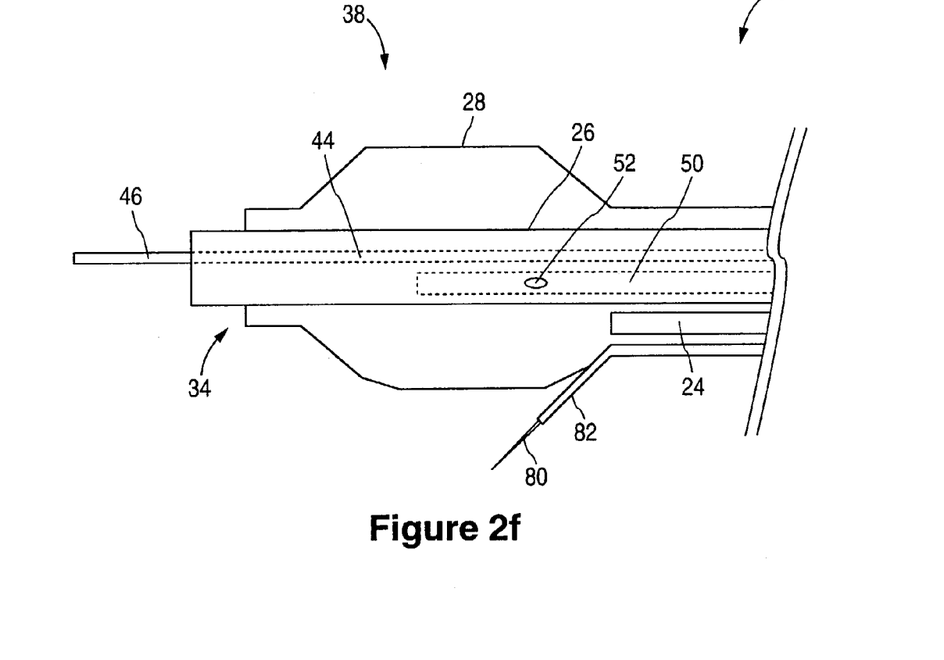
FIG. 2f is a detailed cross-sectional view of the distal portion of the device of FIGS. 2a–2e.

In yet other embodiments of the device, shown in FIGS. 2d and 2e, the inner lumen 22 also serves as the lumen through which fluid flows to inflate and/or deflate the balloon 28. As such, the separate fluid lumen, described above, is omitted from the catheter-based needle drug delivery device 10. Thus, the inner lumen 22 functions as a fluid lumen in addition to housing the guide wire lumen 44 and ultrasonic element lumen 50. Alternatively, the inner lumen 22 functions as a fluid lumen and also contains the guide wire 46 and retractable ultrasonic element 52.

The structure of the inflatable balloon 28 is similar to those well known to those having ordinary skill in the art. The inflatable balloon 28 may be used for various procedures including, but not limited to, opening narrowed passageways, distributing drugs to specific target sites, and delivering/positioning stents or other medical devices within the lumen. The term "target site," as used herein, refers to sites/areas both inside and outside the vessel/lumen. The inflatable balloon 28 is located at the distal end 38 of the device 10 and is initially deployed in a low profile, deflated condition. When the balloon 28 is positioned at the target site it is inflated with fluid via the inflation port 40 located near the proximal end 42 of the device 10. During inflation of the balloon 28, fluid flows from the inflation port 40, through the fluid lumen 24, and to the balloon 28. In addition, the fluid flows through the same lumen 24, but in the opposite direction, upon deflation and subsequent removal of the balloon 28.

Extending partially along the length of the device 10 is the inner member 26. As shown in FIGS. 2a–2e, a portion of the inner member 26 protrudes out the distal end 34 of the balloon 28. Housed within and along the length of the inner member 26 are two lumens. The first lumen 44, i.e. the guide wire lumen, provides a passageway for a movable guide wire 46. The guide wire 46 extends from beyond the distal end 38 of the device 10 to a guide wire exit 48 located near the proximal end 42 of the device 10. The guide wire 46 serves as the steering mechanism of the device 10 and enables an operator to maneuver the device 10 through the various vessels and lumens of the patient to the chosen target site. Overall length and diameter of the guide wire 46 are within the range of approximately 74.8 inch to 118.1 inch (190 cm to 300 cm) and 0.0152 inch to 0.019 inch (0.0386 cm to 0.0483 cm), respectively. The guide wire 46 may be fabricated from a variety of materials including, but not limited to, stainless steel, Nitinol™, platinum and polymers. These and other similar materials exhibit the required structural properties, such as strength and flexibility, desired in guide wire elements 46.

Figure 3:
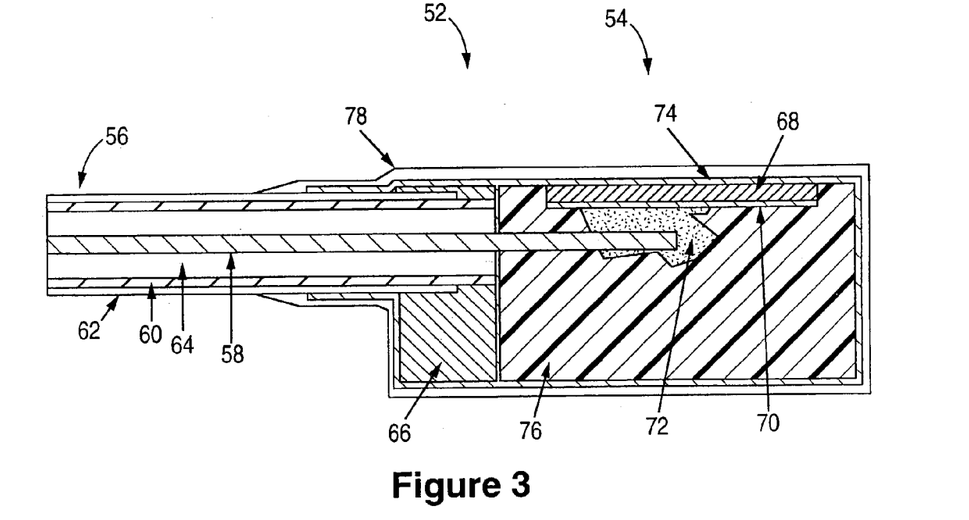
FIG. 3 is a detailed cross-sectional view of the ultrasound transducer of FIG. 2f.

The second lumen 50, i.e. the ultrasonic element lumen, of the inner member 26 houses the retractable ultrasonic element 52 of the device 10. As shown in FIGS. 2b and 3, the distal end of the ultrasonic element 52 has an ultrasound transducer or transducer array 54 and the proximal end contains the associated co-axial cable 56 that connects to the imaging display system 12 (i.e. IVUS imaging system). In general, ultrasonic waves generated by the ultrasonic element 52 impinge on the surface of the target area. The timing/intensity of the ultrasonic waves reflected back to the transducer 54 differentiates between the various anatomic boundaries or structures of the target area. The waves detected by the transducer 54 are converted to electric signals that travel along the coaxial cable 56 to the imaging system 12. The electrical signals are processed and eventually arranged as vectors comprising digitized data. Each vector represents the ultrasonic response of a different angular sector of the target area and/or bodily lumen. As such, the amplitude of the reflected ultrasonic waves/electric signals is displayed as variable shades of, for example, gray on the display. Thus, anatomic structures with different acoustic density are portrayed with varying degrees of brightness, resulting in a visible, displayed image of the various structures within the body.

The coaxial cable 56 of the ultrasonic element 52 contains an insulated solid or stranded center conductor 58 (e.g., a wire) surrounded by a solid or braided metallic shield 60, wrapped in a plastic cover or jacket 62. The wire 58 is the primary conductor, whereas the shield 60 is used for ground. The insulation 64 surrounding the wire 58 is typically made of a dielectric material, such as polyester or plastisol, and functions to sustain the current traveling within the wire 58 with minimal dispersion. A conductive material 66, for example copper, gold, palladium, conductive epoxy, or other similar materials, is used to attach and electrically connect the distal end of the coaxial cable 56 to the ultrasound transducer 54.

The ultrasound transducer 54 has a piezoelectric crystal 68 configured for optimal acoustic output efficiency and energy conversion. In some embodiments, the crystal 68 is made of PZT or lead-ceramic materials, such as $PbTiO_3$ (lead titanate) or $PbZrO_3$ (lead zirconate). As shown in FIG. 3, the back surface 70 of the piezoelectric crystal 68 is coated with conductive material plating such as gold, platinum or palladium, and other similar conductive materials. The gold plating provides a sufficient electrical contact to the back 70 of the piezoelectric crystal 68 to connect with the wire 58 of the coaxial cable 56. A conductive epoxy 72 is used to mechanically and electrically attach or connect the coaxial center conductor 58 to the back 70 of the piezoelectric crystal 68. In addition to conductive epoxy 72, solder joints, cold solders, ultrasonic welds and other similar attachment techniques can also be used.

The front surface 74 of the piezoelectric crystal 68 is also coated with conductive material plating. The front surface plating electrically connects the front surface 74 of the crystal 68 to the coaxial shield 60 through the conductive material 66. Partially surrounding the crystal 68 and its related components is a backing material 76. The backing material 76 serves as a nonconductive sound absorbing material that eliminates sound waves coming off the back 70 of the piezoelectric crystal 68. In addition, the backing material 76 also facilitates rapid reduction in piezoelectric oscillations.

To electrically isolate the ultrasound transducer 54, the transducer 54 is covered in a paralyene coating 78. The paralyene coating 78 is a quarter wave matching layer that does not interfere with the acoustic output or response of the piezoelectric element. In addition, the paralyene electrically isolates the two sides of the piezoelectric crystal and associated electrical connections.

As shown in FIGS. 2a and 2b, the device also includes a retractable needle 80 housed in the needle lumen 82 and freely movable therein. The hollow, tubular shaped needle 80, having an inner diameter within the range of approximately 0.002 inch to 0.010 inch ($5.1 \times 10^{-3}$ cm to $25.4 \times 10^{-3}$ cm) and an outer diameter within the range of approximately 0.004 inch to 0.012 inch ($10.2 \times 10^{-3}$ cm to $30.5 \times 10^{-3}$ cm) provides a fluid conduit that extends from the proximal end 84 to the distal end 86 of the needle 80. The distal end 86 of the needle 80 terminates in a curved, tissue piercing tip having an angle of curvature between 30 degrees to 90 degrees. Needle curvature facilitates placement of the needle tip near to or within the desired target tissue.

Further, to allow easy needle deployment from and retractability into the lumen, yet provide sufficient structural strength for insertion into tissue, the needle 80 is preferably fabricated from, for example, stainless steel, NiTi (nickel titanium), platinum or other similar semi-rigid materials. The needle can also be coated with fluoroscopically opaque materials to enhance its imaging capabilities on the fluoroscope.

Near the proximal end 84 of the needle 80, the needle 80 connects to an adapter 86 that attaches the needle 80 to a needle lock 88 and a needle adjustment puncture knob 90. The needle lock 88 is used to secure the needle 80 in place and prevent further movement of the needle 80 within the lumen once the needle 80 is located in the desired position. A needle adjustment knob 90 controls accurate needle extension out of the distal end of the catheter and depth of penetration into the tissue target. In general, the needle adjustment knob 90 is slidable along a proximal portion of the needle lumen or element 89 housing the needle 80. The element 89 includes various gradations or scalable markings along a portion of its length that correspond to the length of needle 80 extending out from the needle lumen 82. During use, the needle adjustment knob 90, that is also attached to the proximal end of the needle 80, is locked into position at a marking corresponding to the desired length of needle extension from the catheter. The knob 90 is then moved in a distal direction until it butts against the needle lock 88. Movement of the knob 90 also moves the needle 80, so that the predetermined length of needle 80 extends out from the needle lumen 82. The needle lock 88 is then used to secure the needle 80 in place and prevent further movement of the needle 80 within the lumen.

Located near the proximal end 42 of the device 10 is a drug injection port 92. The port 92 provides a connection for various dispensing elements such as a syringe, fluid pump, etc. In addition to drugs, other fluids including, but not limited to, therapeutic agents and diagnostic substances, may also be injected into the port 92 for delivery to the target site. Fluids injected into the port 92 travel through the needle 80 and are dispensed from the distal tip of the needle 80.

In an alternate embodiment, the needle 80 can also be used to aspirate fluid from tissues. A negative pressure or suction is applied at the drug injection port 92. The resulting pressure differential within the lumen 82 of the needle 80 causes tissue fluid to be drawn into the tip of the needle 80. The fluid travels toward the proximal end 84 of the needle 80 and is collected at the injection port 92 site for further analysis.

Method of Use

The retractable ultrasonic element 52 of the drug delivery device 10 allows the various structures located at a target area within a patient's lumen to be imaged and mapped using conventional IVUS technology. The mapped images are used to accurately determine and control the location of the device 10 within the lumen relative to the target area and/or target site. Generally, the target area and/or target site is the narrowed or diseased portion of the lumen requiring drug therapy. Once the drug delivery device 10 is properly positioned within the lumen, additional ultrasonic images are generated and used to control the position and depth of penetration of the retractable needle 80. As such, needle position can be precisely determined, both in relationship to the device 10 as well as the target site for drug delivery. This allows accurate delivery of drug to the target site and, thus, enhanced treatment capabilities.

Figure 4:
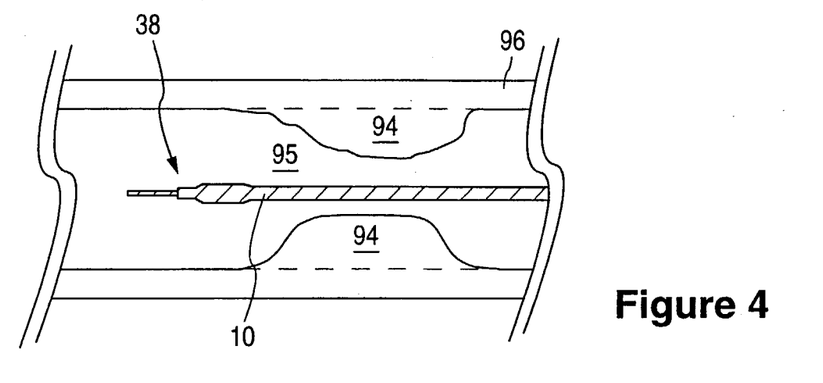
FIG. 4 illustrates one embodiment of the catheter based needle drug delivery device positioned within a lumen.

During use of the device 10, the distal end 38 of the device or catheter 10 is inserted into the lumen of the patient and guided to the target area, i.e. narrowed area due to plaque buildup, via conventional methods. As shown in FIG. 4, the distal end 38 of the catheter 10, in particular the retractable ultrasonic element (not shown), is positioned near the target site 94 of the patient's lumen 96. In one embodiment, the retractable ultrasonic element is positioned distal to the target site 94 of the patient's lumen. The target area 95 is then imaged using IVUS technology. In general, a signal, in the form of a voltage pulse, generated by the signal processor of the IVUS system (not shown) travels through the coaxial cable to the ultrasound transducer of the ultrasonic element. The voltage pulse results in an electromotive force that causes the crystal of the transducer to oscillate, thereby producing sonic waves.

Figure 5:
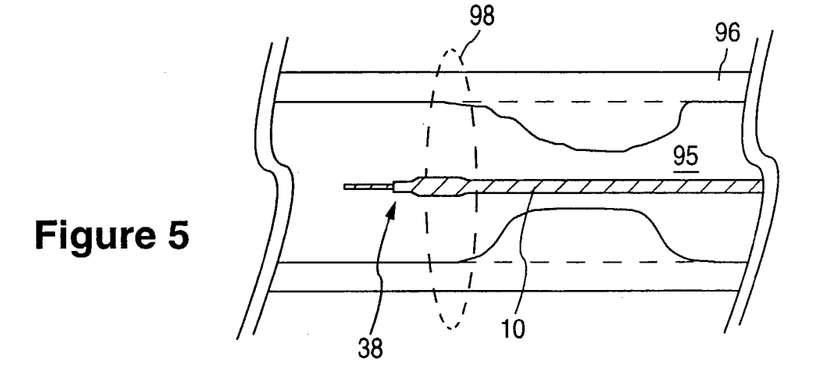
FIG. 5 illustrates the ultrasound field wave generated by the device of FIG. 4.

As shown in FIG. 5, the ultrasonic waves 98, forming an energy waveform field, emanate from the ultrasound transducer (not shown) into the surrounding tissues and structures. Waves reflected by tissues, or other structures in the lumen 96 near the target area 95, and detected by the ultrasound transducer are converted back to electric signals. The signals travel along the coaxial cable to the imaging system where they are then processed. As a result, a first axial, cross-sectional image of the various structures is generated and displayed on the IVUS system. The image that appears on the display is then adjusted and optimized, in terms of gain, zoom, and other related resolution variables.

Figure 6:
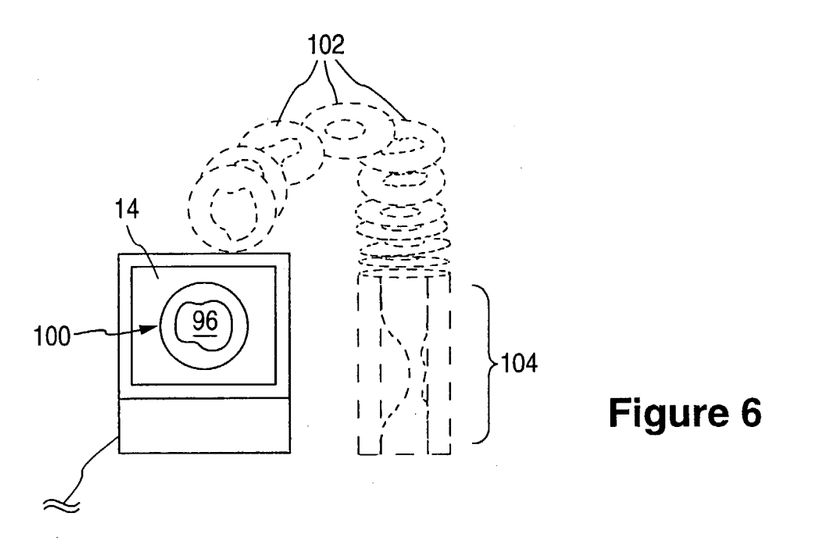
FIG. 6 illustrates one embodiment of the display, imaging and stacking functions of an IVUS system.

To obtain a mapped, longitudinal view of the lumen 96, the distal end of the ultrasonic element 52 is slowly moved in the proximal direction. Movement of the ultrasonic element 52 may be either manually and/or automatically controlled. Approximately hundreds of cross-sectional images are generated, similar to the above-described single-image procedure, and then stacked in real time. FIG. 6 representatively illustrates the imaging and stacking functions performed by an IVUS system. A single, cross-sectional image 100 of a lumen 96 is displayed on the monitor 14. Additional cross-sectional images 102, generated as the ultrasonic element 52 (not shown) is slowly moved through the lumen, are shown in hatched lines. These images 102 are collected and processed, or stacked, by the system in real-time mode. The developing longitudinal view 104 of the lumen 96 (also shown in hatched lines) as the ultrasonic element 52 is moved through the lumen 96 can also be displayed on the monitor 14 of the IVUS system. Therefore, the IVUS system can either display a two-dimensional cross-sectional image of the lumen 96 or a three-dimensional longitudinal view of the lumen 96.

Figures 7, 8:
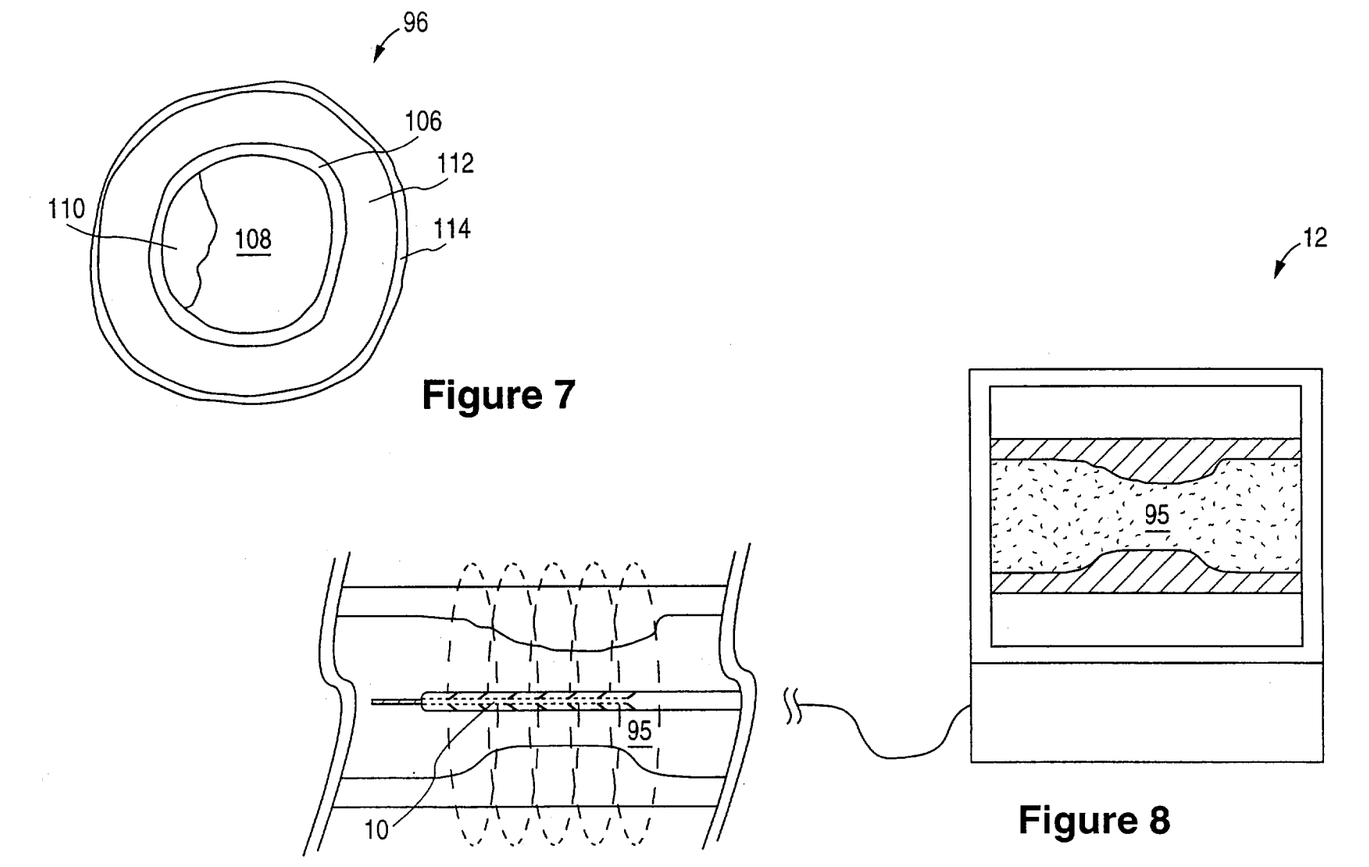
FIG. 7 is a cross-sectional view of a lumen.
FIG. 8 illustrates a method of using the device of FIG. 4.

In general, a vascular or arterial image consists of three layers that make up the walls of the lumen 96. As shown in FIG. 7, the inner-most radial layer 106, which, for example, surrounds the hollow channel 108 of the lumen 96 through which blood flows, contains endothelial cells. White blood cells migrate from the bloodstream into the endothelial cells of the lumen 96 and are transformed into cells that accumulate fatty materials. The accumulated materials 10, also termed plaque, continue to build within the lumen. As the plaque 110 thickens, the channel 108 within the lumen 96 narrows. The plaque 110 may further occlude the lumen 96 until it is completely closed or it may detach and float downstream, causing an obstruction elsewhere.

Surrounding the endothelial cells is a layer of smooth muscle cells 112. In addition to reducing the lumen opening 108, the plaque 110 may also stimulate smooth muscle growth 112. Proliferation of smooth muscle cells 112 further contributes to decreasing the size of the lumen opening 108. The outermost layer 114 of the lumen 96 is termed the adventitia. In general, the function of the adventitia is to provide nutrients to the vessel wall.

In an alternate embodiment, the internal lumen 96 may also be imaged by initially positioning the tip of the ultrasonic element 52 proximal to the target area 95. As such, a longitudinal view of the lumen 96 may be obtained by slowly pushing the ultrasonic element 52 in the distal direction until the tip of the ultrasonic element 52 is located distal to the target area 95. In another embodiment, the ultrasonic element 52 is pushed and/or pulled repeatedly across the target area 95 to obtain numerous detailed images and views of the lumen 96 and structures within the lumen 96. Other areas or structures of interest within the lumen 96 may also be investigated using the methods described above.

In addition to displaying the internal surface of the lumen 96, the device 10 is also used to accurately determine catheter position with respect to the target site 94 within the lumen. In addition to specifically targeting the desired regions of the lumen 96, the transducer 54 is also used to accurately track the position and location of the retractable needle 80. Therefore, both the exact location and depth of needle penetration are determined with the device 10.

By imaging the target area 95 of the lumen 96, a user of the device is able to precisely identify the desired injection site. As previously explained, angiogenesis, restenotic drug therapies and other related procedures require injections of various fluids including, but not limited to, therapeutic agents, diagnostic reagents, and genetic material, whereby the fluids are delivered directly to the diseased area of the lumen 96. Ultrasonic imaging enables device users to track needle movement and penetration into tissue.

Figure 9:
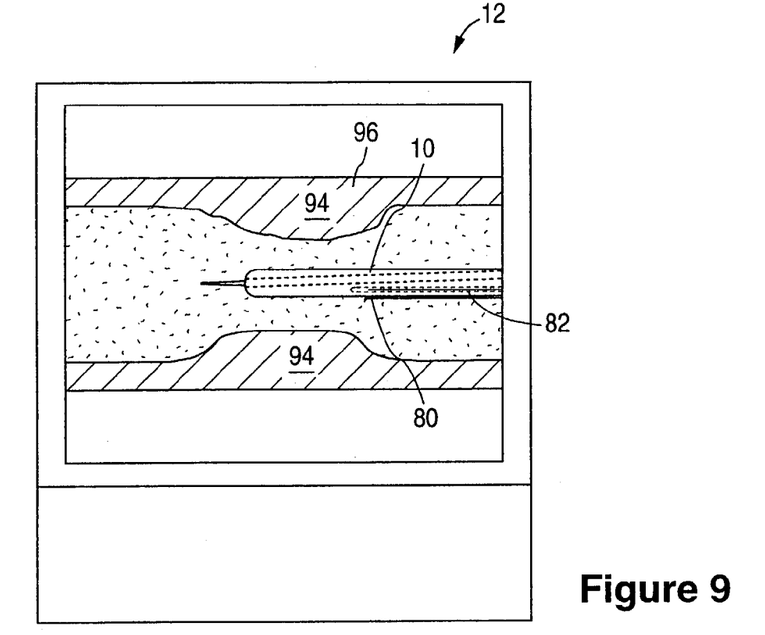
FIG. 9 illustrates one embodiment of the image of the lumen and device of FIG. 4.

The imaging technique requires an initial imaging of the target area 95. As shown in FIG. 8, the retractable ultrasound element (not shown) of the device 10 maps the inner surface of the target area 95 adjacent to the balloon (not shown) with the aid of a conventional IVUS system 12. In addition, the position of the retractable needle (not shown) is also mapped using the same ultrasound element and IVUS system 12. FIG. 9 illustrates one image of the catheter 10 and retractable needle 80 within the lumen 96 as mapped using the ultrasound technique. The differential density between the needle material and the target tissue results in a discrete and easily identifiable IVUS signal. As such, needle position can be precisely determined, both in relationship to the host catheter 10 as well as the target site 94 for drug delivery.

Figure 10:
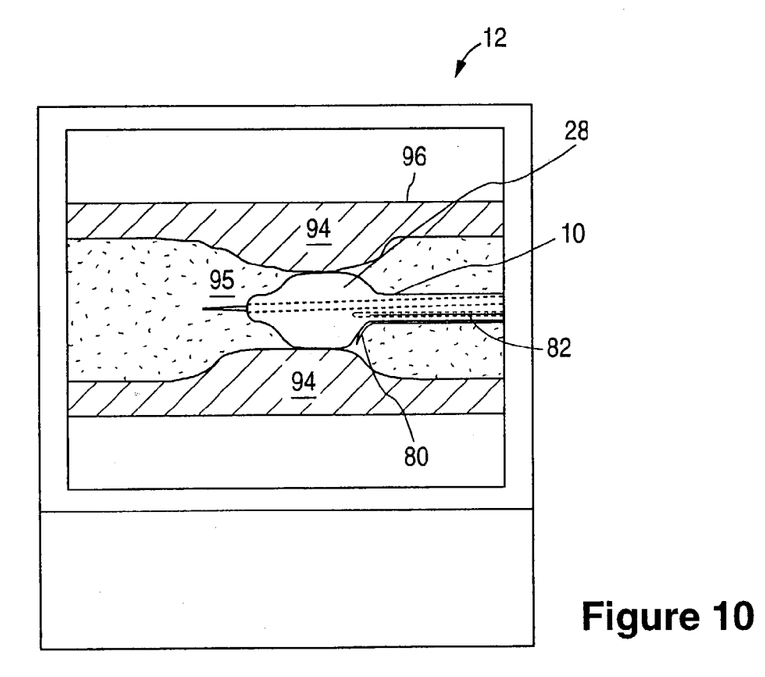
FIG. 10 illustrates an alternate embodiment of the image of the lumen and device of FIG. 4.
Figure 11:
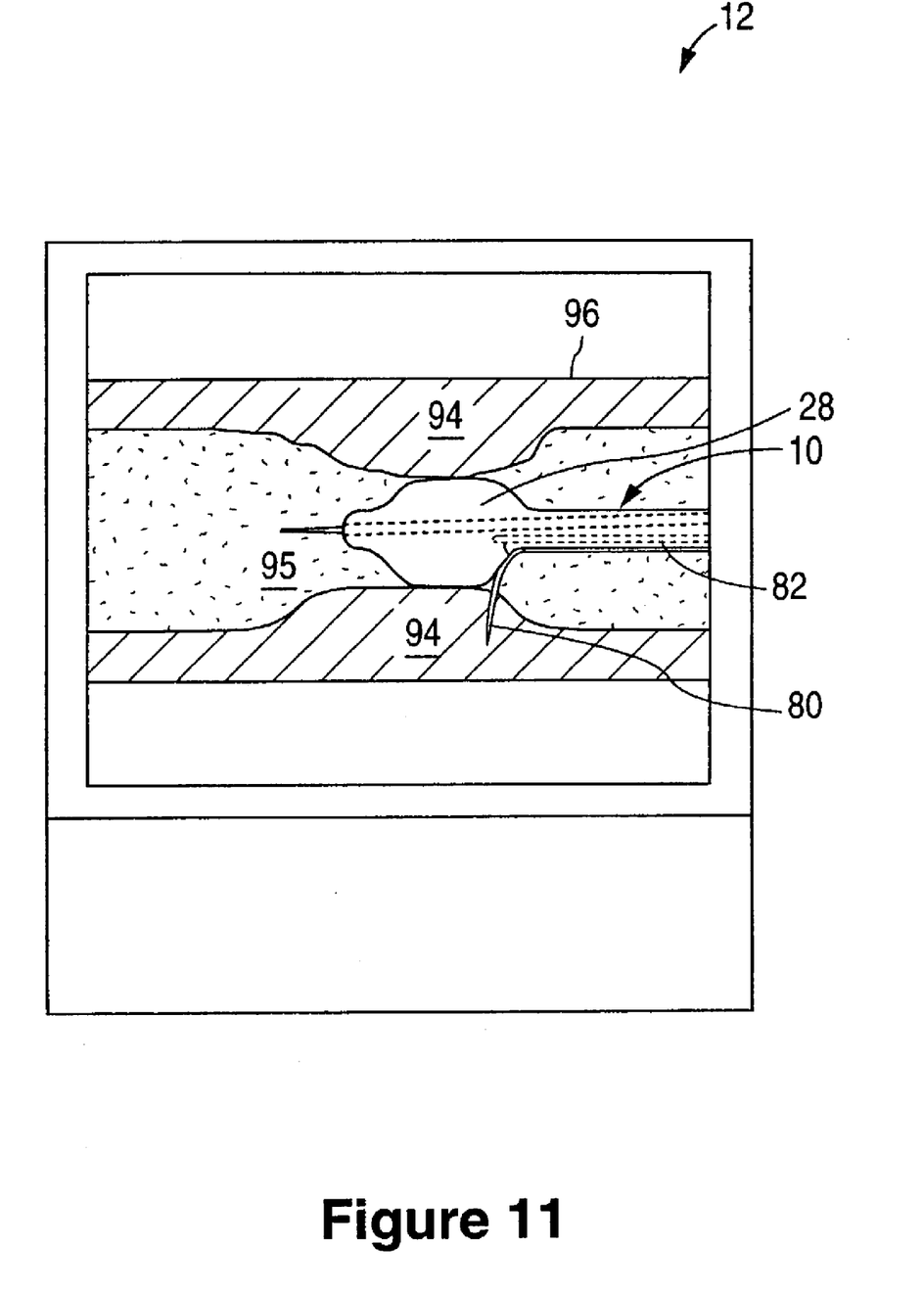
FIG. 11 illustrates another embodiment of the image of the lumen and device of FIG. 4.

Since the size of the catheter 10 and its components are known, accurate calculations and measurements can be made of the structures within the lumen 96. When the needle 80 is optimally positioned at the target site 94, the balloon 28 is inflated with fluid. As shown in FIG. 10, the inflated balloon 28 securely situates the catheter 10, and thereby the needle 80, within the lumen 96. The inflated balloon 28 also prevents the catheter 10 from sliding out of position when the needle 80 is inserted into the tissue. In general, as the needle 80 is advanced out of the needle lumen 82 and contacts the tissue surface, the resistance of the tissue to needle penetration has a tendency to force the associated catheter 10 in a direction approximately opposite to the direction of needle advancement/penetration. However, the friction between the inflated balloon 28 contacting the tissue surfaces prevents movement of the catheter 10 in the opposite direction. Due to the added support from the balloon 28, the needle 80 is allowed to advance and thereby penetrate the tissue. As shown in FIG. 11, the depth of needle penetration can be easily calculated using the ultrasonic image. As such, the needle 80 can be extended a predetermined depth into the tissue and/or target site 94. This allows accurate delivery of, for example, drug to the target area 95 and, thus, enhanced treatment capabilities.

After the desired amount of drug is delivered to the target site 94, the needle 80 is retracted and removed from the tissue. The fluid is also removed from the balloon 28 so that the balloon 28 returns to a low profile, deflated state. At this point, the device 10 may be repositioned at an alternate target site 94 for additional drug delivery according to the above-described procedure. Alternatively, upon completion of the procedure, the device 10 may simply be removed from the lumen 96 of the patient.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of delivering a drug directly to a target site comprising:
    positioning a retractable ultrasonic element of a drug delivery device at said target area in a lumen;
    generating a real-time image of said target area using said retractable ultrasonic element and an IVUS system;
    determining a location of said target site from said image;
    locating said drug delivery device at said target site, whereby a balloon of said drug delivery device is inflated to fixedly secure said device at said target site;
    extending a retractable needle of said drug delivery device so that said needle penetrates said target site;
    tracking said needle movement and depth of penetration into said target site using said retractable ultrasonic element and said IVUS system; and
    extending said retractable needle a predetermined depth into said target site for dispensing drug directly to said target site.

2. The method of claim 1 wherein said act of generating a real-time image of said target area comprises locating said retractable ultrasonic element distal to said target area and slowly moving said element in a proximal direction so that approximately hundreds of cross-sectional images are generated and then stacked in real time using said IVUS system.

3. The method of claim 1 wherein said act of generating a real-time image of said target area comprises locating said retractable ultrasonic element proximal to said target area and slowly moving said element in a distal direction so that approximately hundreds of cross-sectional images are generated and then stacked in real time using said IVUS system.

4. The method of claim 1 wherein said act of locating said drug delivery device at said target site comprises mapping an inner surface of said target area adjacent to said balloon and mapping a position of said retractable needle using said retractable ultrasound element and said IVUS system.

5. The method of claim 1 wherein said act of tracking said needle movement and depth of penetration into said target site comprises repeatedly pushing and/or pulling said ultrasonic element across said target area to obtain numerous detailed images that are displayed on said IVUS system.

6. The method of claim 1 whereby said image is a two-dimensional cross-sectional image.

7. The method of claim 1 whereby said image is a three-dimensional longitudinal view.

* * * * *